United States Patent [19]

Hagiwara et al.

[11] Patent Number: 5,320,849
[45] Date of Patent: Jun. 14, 1994

[54] ANTI-VIRUS AGENT

[75] Inventors: Katsushi Hagiwara, Kakogawa; Mikio Kikuchi, Chigasaki, both of Japan

[73] Assignee: Taito Co., Ltd., Tokyo, Japan

[21] Appl. No.: 28,624

[22] Filed: Mar. 8, 1993

Related U.S. Application Data

[63] Continuation of Ser. No. 719,501, Jun. 24, 1991, abandoned.

[30] Foreign Application Priority Data

Jun. 25, 1990 [JP] Japan .................. 2-166251

[51] Int. Cl.$^5$ .................................. A23K 1/165
[52] U.S. Cl. ........................ 424/442; 424/451; 424/464; 424/480; 424/489; 424/494; 514/54; 514/888; 536/120
[58] Field of Search .......... 424/442, 480, 494, 489, 424/451, 464; 514/54, 888

[56] References Cited

U.S. PATENT DOCUMENTS

| | | | |
|---|---|---|---|
| 3,943,247 | 3/1976 | Komatsu et al. | 514/25 |
| 4,645,757 | 2/1987 | Hjerten et al. | 514/54 |
| 4,859,769 | 8/1989 | Karlsson et al. | 514/25 |
| 5,053,398 | 10/1991 | Mon et al. | 514/54 |

FOREIGN PATENT DOCUMENTS

| | | |
|---|---|---|
| 0384323 | 2/1990 | European Pat. Off. . |
| 2329290 | 5/1977 | France . |
| 287031 | 11/1989 | Japan . |
| 218615 | 8/1990 | Japan . |
| 8912106 | 12/1989 | PCT Int'l Appl. . |

OTHER PUBLICATIONS

Chemical Abstracts, vol. 96, No. 11, Mar. 15, 1982, p. 28, Abstract No. 79475x, Columbus, Ohio, US; Y. Hiyama et al: "Antiviral Activity of Schizophyllan (SPG), An Antitumor Polysaccharide", & Kinki Daigaku Igaku Zasshi 1981, 6(3), 387-91.
Patent Abstracts of Japan, vol. 14, No. 526 (C-779)[4469], Nov. 19, 1990, p. 54; & JP-A-2 218 615 (Taito K.K.) Aug. 31, 1990 Int. J. Immunopharmac., vol. 12, No. 2, pp. 225-233 (1990).
Stryer, "Biochemistry", 3rd Ed., W. H. Freeman and Co., New York (1988), pp. 202 and 852.
Lechninger, "Biochemistry", 2nd Ed., Worth Publishers, Inc. New York (1975), pp. 268-271.

Primary Examiner—Thurman K. Page
Assistant Examiner—Jyothsna Venkai
Attorney, Agent, or Firm—Oblon, Spivak, McClelland, Maier & Neustadt

[57] ABSTRACT

An oral anti-virus agent containing a polysaccharide having the following chemical structure as an active component,

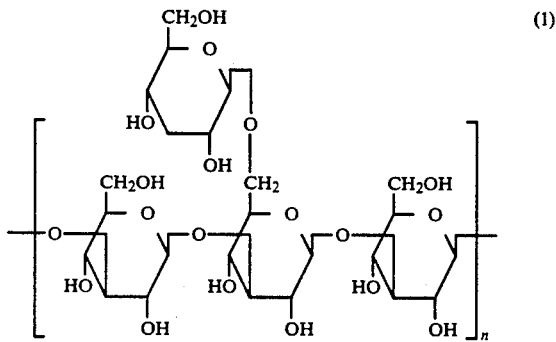

(wherein n is an integer of at least 16).

20 Claims, No Drawings

ANTI-VIRUS AGENT

This application is a continuation of application Ser. No. 07/719,501, filed on Jun. 24, 1991, now abandoned.

The present invention relates an oral anti-virus agent containing as an effective ingredient a polysaccharide having a chemical structure comprising the repeating unit as expressed by the formula (1).

There are various diseases caused by viruses. However, a living body infected with a virus is not always suffered from a disease. The outbreak of an infectious virus disease depends on such factors as the amount of virus, the intensity of toxicity and the immune system-enhancing ability of the infected person.

At present, methods for treating a virus disease are classified into the following two groups.

(i) A method for treating a virus disease by controlling the immune system-enhancing ability of an infected person, and (ii) A method for treating by directly acting on a virus.

A typical example of the former method is a preventive method using a vaccine.

Heretofore, various infectious virus diseases such as small pox, yellow fever and polio have been treated with vaccines. The common characteristics of these types of viruses are that the surface structures of the outer shells of the viruses hardly vary. Therefore, the aimed effect could be expected by preparing one type of vaccine for one type of virus. However, it is considered that it is very difficult to control a virus, the surface structure of which often varies, with a vaccine alone.

Recently, infectious virus diseases such as AIDS (Acquired Immunodeficiency Syndrome), ATL (Adult T cell Leukemia) or hepatitis B disease became a social problem, but it is substantially impossible to treat these infectious virus diseases with a vaccine only. Therefore, pharmaceuticals having functions such as adsorption inhibition to virus cells, inhibition of reverse transcriptase or inhibition of protein synthesis are used as anti-virus agents, and at the same time developments and researches are now being made to seek for more improved anti-virus agents. These methods correspond to the latter method among the above-mentioned treating methods for virus diseases, but it has been reported that liver troubles, hypersensitiveness, vitamin deficiency, central nerve troubles and the like are caused. Besides, viruses, to which these pharmaceuticals are effective, are limited.

Now, it has been developed to achieve anti-virus effects by activating immune system-enhancing ability of an infected person Thus, various immune system-enhancing materials have been already known, but interferon among them is used as an anti-virus agent. Although interferon can be expected to have an effect on various virus since it has a function for activating immune system-enhancing ability, there are various problems that the specificity of an infected person is revealed and that the effect is reduced by continuous administration.

We have discovered that the specific polysaccharide activates immune system-enhancing ability in the same manner as interferon when it is administered into a living body and that it achieves a remarkable anti-virus effect on various viruses. The present invention has been accomplished on the basis of this discovery.

As the polysaccharides, there can be enumerated schizophyllan produced by *Schizophyllum commune* Fries, scleroglucan produced by *Sclerotium glucanicum* and pendulan produced by *Porodisculus pendulus*. These homopolysaccharides can be extracellularly produced by culturing the respective strains. The polysaccharide obtained by such culturing forms an extremely viscous and thixotropic aqueous solution, and its purification by filtering, decoloring or deashing operation is usually difficult. To purify such polysaccharide to a high degree so that it may be used as a pharmaceutical intended by the present invention, it is advisable to lower the molecular weight by the depolymerization of the polysaccharide. Such depolymerization may preferably be conducted by irradiating ultrasonic waves to the aqueous polysaccharide solution or treating such polysaccharide solution with a high shear force. By such depolymerization, only the main chains composed of $\beta$-1,3-glucoside bonds of the polysaccharide, are selectively cleaved, and the side chains composed of $\beta$-1,6-glucoside bonds remain substantially uncleaved.

Thus, the fundamental structure of the polysaccharide will be remained unchanged even after the depolymerization.

The polysaccharide used in the present invention is a polysaccharide containing $\beta$-1,3-linked backbone chain. Therefore, as opposed to polysaccharides having $\alpha$-glucoside bonds, such as starch or dextran, it is scarcely decomposed by enzymes in the living body and has very little toxicity as its feature.

One of the polysaccharides, schizophyllan is known to have an anti-cancer activity based on immune system-enhancing action, and was approved in Japan as a drug for an anti-cancer agent. Schizophyllan is known also to have an anti-virus action against influenza virus by intramuscular administration or intraperitoneal administration. ("Medical Journal" by Kinki University, vol. 6, No. 3, p. 387–391, 1981)

Generally, the polysaccharides and their similar anti-tumor materials have high molecular weights, and therefore they are usually administered into a living body by injection. The effectiveness of these materials by oral administration has been tested in view of clinical convenience but there has been no report that these materials are effectively absorbed in a living body by oral administration.

Thus, when these materials are orally administered, there is a tendency that internal lymph corpuscle subset is varied or the proliferation of tumor is somewhat inhibited by the activation of immune system-enhancing ability, but there is no report that these materials orally administered are effective for clinical cancer treatment.

Furthermore, in view of a slight immune system-enhancing effect achieved by oral administration, the polysaccharides have been used as a food to utilize their physiological functions. However, it is a common sense that neutral polysaccharides are hardly absorbed into intestines. ("Shokuhin Kako Gijutsu" (Food Processing Technique) vol. 18, No. 4, p.271, 1988) ("Kagaku to Seibutsu" (Chemistry and Organism) vol. 25, No. 4, p. 273, 1987).

Under these circumstances, with regard to physiological function of the polysaccharides, the study has been continued mainly with internal administration by injection.

On the other hand, as mentioned above, with regard to an effect achieved by one of the polysaccharides, i.e. schizophyllan, on anti-influenza virus, an effectiveness achieved by intramuscular or intraperitoneal administration by injection was generally known, but an effectiveness by oral administration of the polysaccharides was not substantially recognized in clinical practical use since various anti-inflammatory agents and antibiotics by oral administration are widely used against influenza virus.

Under these circumstances, the present inventors have made a research aiming that an anti-virus activity by the polysaccharides can be effective for practical use even by oral administration, and as the result of this research, contrary to common opinion, they have discovered that the polysaccharides achieve an anti-virus effect sufficiently effective for clinical use even by oral administration.

It is considered that the anti-virus effect by the polysaccharides in the present invention can be achieved by activating cells in charge of immune system of a living body and by making efficient use of non-specific immune system-enhancing function, but more detailed mechanism of achieving the effect by oral administration is not clear at present.

Thus, the anti-virus agent of the present invention is characterized by being effected by oral administration, and achieves an anti-virus effect, particularly preventive effect against various pathogenic viruses including influenza virus, herpes virus, Sendai virus, SSPE virus and the like. However, a treatment effect against AIDS is not recognized.

The polysaccharides of the present invention are hardly decomposed by internal digestive enzymes, and their toxicity is remarkably low. Besides, they do not exhibit any side effect even by injection administration. Thus, the polysaccharides have excellent characteristics that their toxicity when orally administered is almost zero.

Since the polysaccharides of the present invention are natural products and non-toxic, an anti-virus effect can be sufficiently expected even when they are incorporated in foods or feeds for animals.

As mentioned before, it is desired to reduce the molecular weights of the polysaccharides to a certain extent (not higher than 1,000,000) when they are purified as drugs. On the other hand, when they are incorporated in foods or feeds, it is not necessary to strictly purify the polysaccharides and their crude products or dried products of culture liquor used in the production of the polysaccharides can be effectively used.

There are some known water-soluble or water-insoluble polysaccharides having side chains branched by $\beta$-1,6-glucoside bonds in the structure as shown in the formula (1), the branched degree of which is different from those of the polysaccharides of the present invention. In addition to these polysaccharides having $\beta$-1,3-glucoside bonds in the main chains, yeast glucan and mannan having immune system-enhancing activities are recognized to have anti-virus activities similar to those of the polysaccharides of the present invention. However, according to the study of the present inventors, their effects can not be sufficiently confirmed due to scattering of test data.

Mycelium of the schizophyllan-producing fungus, *Schizophyllum commune* Fries, is known to contain waterinsoluble polysaccharides such as glucans consisting essentially of main chains of $\beta$-1,3-glucoside bonds and $\beta$-1,6-glucoside side chains, but their structures are complicated and have not been elucidated (J. G. H. Wessels, et al. Biochimica et Biophysica Acta, 273, 346–358 [1972]).

Polysaccharides in the mycelium of *Schizophyllum commune* Fries may also have similar effects on anti-virus activities because pulverized mycelium of the schizophyllan-producing fungus exhibits anti-virus activities by oral administration.

Now, the present invention will be described in further detail with reference to Examples. However, it should be understood that the present invention is by no means restricted to such specific Examples.

The polysaccharides of the present invention can be used in various dosage forms such as tablets, granules and suspensions, and various additives are added to active components.

In the preparation of tablets, additives such as lactose, crystalline cellulose, hydroxypropylcellulose, carboxymethylcellulose and the like are generally used, and the content of the polysaccharides is generally from 10 to 100 mg/tablet (500 mg), i.e. from 2 to 20% by weight.

In the preparation of granules, additives such as lactose, crystalline cellulose and the like are generally used, and the content of the polysaccharides is generally from 20 to 200 mg/g, i.e. from 2 to 20% by weight.

In the preparation of suspensions, additives such as sucrose, polysorbate 80, sodium carboxymethylcellulose and the like are generally used, and the content of the polysaccharides is generally from 2 to 20 mg/ml.

When the polysaccharides of the present invention are added to a food or an animal feed, they are added in an amount of from 0.1 to 10 g/kg, i.e. from 0.01 to 1% by weight.

EXAMPLE 1

Schizophyllan (molecular weight: 460,000), scleroglucan and pendulan were compulsorily orally administered respectively into mice with a catheter (150 mg/kg/each time) seven times in total, i.e. 5 days before, 4 days before, 3 days before, 2 days before and one day before the virus infection, and the first day after and the second day after the virus infection. The mice were infected with influenza virus (2 $LD_{50}$) through their noses. The mice used for the tests were ICR type (male, 3 weeks old, weight: $10\pm1$ g) mice and ten mice were used in a group.

In the same manner as in the above Examples, Isoprinosine (trade name for inosine pronobex) was orally administered (400 mg/kg/each time) as a positive control seven times in total.

As this result, nine of the ten non-administered mice were dead by the 15th day after the virus infection, and seven of the ten Isoprinosine-administered mice were survived even after 31 days from the virus infection. Eight of the ten schizophyllan-administered mice, seven of the ten scleroglucan-administered mice and seven of the ten pendulan-administered mice were respectively survived. Mean surviving days were determined on the assumption that all the examples were dead on the 31st day after the virus infection, and T/C values (the values obtained by dividing mean surviving days of each administration group by mean surviving days of nonadministration group) were also determined.

As can be seen from the following Table 1, the administration of the polysaccharides of the present invention significantly improves surviving rate and extends surviving days as compared with the nonadministration group.

TABLE 1

| Polysaccharides | Anti-influenza virus effects by polysaccharides | | | | |
| --- | --- | --- | --- | --- | --- |
| | Mean surviving days (Mean ± S.D.) | Surviving rate (%) | $x^2$ - test | T/C | t - test |
| No administration | 14.3 ± 6.2 | 10 | — | 1.00 | |
| Schizophyllan | 28.0 ± 6.4 | 80 | $P < 0.01$ | 1.96 | $P < 0.01$ |
| Scleroglucan | 26.9 ± 6.7 | 70 | $P < 0.05$ | 1.88 | $P < 0.01$ |
| Pendulan | 26.7 ± 6.9 | 70 | $P < 0.05$ | 1.87 | $P < 0.01$ |
| Isoprinosine | 26.9 ± 6.8 | 70 | $P < 0.05$ | 1.88 | $P < 0.01$ |

EXAMPLE 2

Schizophyllan (molecular weight: 460,000), scleroglucan and pendulan were administered in the same manner as in Example 1, and mice were infected with herpes (2 $LD_{50}$) by intraperitoneal injection. The mice used for the tests were C3H/HeN, Crj (weight: 20±1 g) and ten mice were used in a group. Acyclovir was orally administered (200 mg/kg/each time) as a positive control in the same manner as in the above Examples.

As this result, eight of the ten non-administered mice were dead by the 14th day after the virus infection, but seven of the ten schizophyllan-administered mice, six of the ten scleroglucan-administered mice and five of the ten pendulan-administered mice were respectively survived even after 24 days from the virus infection. In the case of acyclovir, seven of the ten acyclovir-administered mice were survived.

In the same manner as in Example 1, mean surviving days and surviving rate were determined, and the results are shown in the following Table 2. As this result, it was recognized that schizophyllan exhibited the same degree of anti-virus effect as acyclovir.

TABLE 2

| Polysaccharides | Anti-herpes virus effects by polysaccharides | | | | |
| --- | --- | --- | --- | --- | --- |
| | Mean surviving days (Mean ± S.D.) | Surviving rate (%) | $x^2$ - test | T/C | t - test |
| No administration | 11.2 ± 7.1 | 20 | — | 1.00 | |
| Schizophyllan | 19.9 ± 6.6 | 70 | $P < 0.10$ | 1.78 | $P < 0.05$ |
| Scleroglucan | 18.4 ± 7.3 | 60 | N.S | 1.64 | $P < 0.05$ |
| Pendulan | 17.4 ± 7.1 | 50 | N.S | 1.55 | N.S |
| Acyclovir | 19.8 ± 6.8 | 70 | $P < 0.10$ | 1.77 | $P < 0.05$ |

EXAMPLE 3

The same tests as in Example 1 were repeated with regard to mice infected with Sendai virus (5 $LD_{50}$) through their noses.

As this result, all of the non-administered mice were dead by 8th day after the virus infection, but six of the ten schizophyllan-administered mice, five of the ten scleroglucan-administered mice and four of the ten pendulan-administered mice were survived even after 14 days from the virus infection. On the other hand, five of the ten Isoprinosine-administered mice were survived after 14 days from the virus infection.

Means surviving days and surviving rate by the 14th day after the virus infection were determined in the same manner as in Example 1, and the results are shown in the following Table 3. As this result, it was recognized that the polysaccharides of the present invention achieved the same degree of anti-virus effects as Isoprinosine.

TABLE 3

| Polysaccharides | Anti-Sendai virus effects by polysaccharides | | | | |
| --- | --- | --- | --- | --- | --- |
| | Mean surviving days (Mean ± S.D.) | Surviving rate (%) | $x^2$ - test | T/C | t - test |
| No administration | 6.6 ± 1.7 | 0 | — | 1.00 | |
| Schizophyllan | 11.6 ± 3.2 | 60 | $P < 0.05$ | 1.76 | $P < 0.05$ |
| Scleroglucan | 12.0 ± 2.7 | 50 | $P < 0.05$ | 1.82 | $P < 0.05$ |
| Pendulan | 10.4 ± 3.5 | 40 | $P < 0.10$ | 1.58 | $P < 0.05$ |
| Isoprinosine | 11.8 ± 2.6 | 50 | $P < 0.05$ | 1.79 | $P < 0.05$ |

EXAMPLE 4

The same tests as in Example 1 were repeated with regard to mice infected with SSPE (Subacute Sclerosing Panencephalitis) virus (5 $LD_{50}$) in their brains.

As this result, all of the non-administered mice were dead by 21st day after the virus infection, but five of the ten schizophyllan-administered mice, three of the ten scleroglucan-administered mice and three of the ten pendulan-administered mice were survived even after 30 days from the virus infection. On the other hand, four of the ten Isoprinosine-administered mice were survived after 30 days from the virus infection.

In the same manner as in Example 1, mean surviving days and surviving rate were determined by 30th day after the virus infection, and the results are shown in the following Table 4. As this result, it was recognized that schizophyllan achieved the same degree of anti-virus effect as Isoprinosine.

TABLE 4

| Polysaccharides | Anti-SSPE virus effects by polysaccharides | | | | |
| --- | --- | --- | --- | --- | --- |
| | Mean surviving days (Mean ± S.D.) | Surviving rate (%) | $x^2$ - test | T/C | t - test |
| No administration | 15.3 ± 3.6 | 0 | — | 1.00 | |
| Schizophyllan | 26.5 ± 4.5 | 50 | $P < 0.05$ | 1.73 | $P < 0.01$ |

TABLE 4-continued

| Anti-SSPE virus effects by polysaccharides | | | | | |
|---|---|---|---|---|---|
| Polysaccharides | Mean surviving days (Mean ± S.D.) | Surviving rate (%) | $x^2$ - test | T/C | t - test |
| Scleroglucan | 24.1 ± 5.3 | 30 | N.S | 1.58 | $P < 0.01$ |
| Pendulan | 24.6 ± 5.3 | 30 | N.S | 1.61 | $P < 0.01$ |
| Isoprinosine | 26.0 ± 4.6 | 40 | $P < 0.10$ | 1.70 | $P < 0.01$ |

EXAMPLE 5

1 kg of culture broth obtained by cultivating *Schizophyllum commune* Fries was homogenized as it was, and the mycelium was fractured and subjected to vacuum drying at 40° C. to obtain 30 g of light yellow dry powder. This dry powder contained 35.1% of schizophyllan, 50.5% of mycelium, 6.2% of water content and 6.7% of ash content.

The dry powder of this culture broth, schizophyllan (molecular weight: 460,000), scleroglucan and pendulan were orally administered into mice infected with Sendai virus (5 $LD_{50}$) in the same manner as in Example 1.

As this result, all of the non-administered mice were dead by the 10th day after the virus infection, but five of the ten schizophyllan-administered mice, four of the ten scleroglucan-administered mice, four of the ten pendulan-administered mice and eight of the ten culture broth dry powder-administered mice were survived even after 14 days from the virus infection. On the other hand, six of the ten Isoprinosine-administered mice were survived after 14 days from the virus infection.

In the same manner as in Example 1, mean surviving days and surviving rate by the 14th day after the virus infection were determined, and the results are shown in the following Table 5. As this result, it was recognized that the dry powder of the culture broth achieved an anti-virus effect in the same manner as schizophyllan.

TABLE 5

| Anti-Sendai virus effects by dry powder of culture broth | | | | | |
|---|---|---|---|---|---|
| Polysaccharides | Mean surviving days (Mean ± S.D.) | Surviving rate (%) | $x^2$ - test | T/C | t - test |
| No administration | 6.4 ± 1.9 | 0 | — | 1.00 | |
| Schizophyllan | 10.8 ± 3.5 | 50 | $P < 0.05$ | 1.69 | $P < 0.01$ |
| Scleroglucan | 11.2 ± 2.8 | 40 | $P < 0.10$ | 1.75 | $P < 0.01$ |
| Pendulan | 11.5 ± 2.7 | 40 | $P < 0.10$ | 1.80 | $P < 0.01$ |
| Dry powder of culture broth | 12.5 ± 3.2 | 80 | $P < 0.01$ | 1.95 | $P < 0.01$ |
| Isoprinosine | 11.1 ± 4.6 | 60 | $P < 0.05$ | 1.73 | $P < 0.01$ |

We claim:

1. A method of treating a virus disease, comprising orally administering an anti-viral agent in an anti-virally effective amount to a patient in need thereof, wherein said agent is a polysaccharide selected from the group consisting of schizophyllan produced by *Schizophyllum commune* Fries, scleroglucan produced by *Sclerotium glucanicum* and pendulan produced by *Porodisculus pendulus*, said polysaccharide is present in a pharmaceutically acceptable carrier in the form of a tablet or granule in an amount of from 2 to 20% by weight of the combination of said polysaccharide and said pharmaceutically acceptable carrier, and said virus is selected from the group consisting of an influenza virus, a herpes virus, a Sendai virus and subacute sclerosing panencephalitis virus.

2. The method according to claim 1, wherein the polysaccharide is schizophyllan.

3. The method according to claim 1, wherein the polysaccharide is scleroglucan.

4. The method according to claim 1, wherein the polysaccharide is pendulan.

5. The method of claim 1, wherein said combination of said polysaccharide and said pharmaceutically acceptable carrier is in the form of a granule.

6. The method of claim 1, wherein said virus is said influenza virus.

7. The method of claim 1, wherein said virus is said herpes virus.

8. The method of claim 1, wherein said virus is said Sendai virus.

9. The method of claim 1, wherein said virus is said subacute sclerosing panencephalitis virus.

10. A method of treating a virus disease, comprising orally administering an anti-viral agent in an anti-virally effective amount to a patient in need thereof, wherein said agent is a polysaccharide selected from the group consisting of schizophyllan produced by *Schizophyllum commune* Fries, scleroglucan produced by *Sclerotium glucanicum* and pendulan produced by *Porodisculus pendulus*, said polysaccharide is present in a food or animal feed in an amount of from 0.01 to 1% by weight, and said virus is selected from the group consisting of an influenza virus, a herpes virus, a Sendai virus and subacute sclerosing panencephalitis virus.

11. The method of claim 10, wherein said combination of said polysaccharide and said pharmaceutically acceptable carrier is in the form of a tablet.

12. The method of claim 10, wherein said polysaccharide is present in said food in an amount of from 0.01 to 1% by weight.

13. The method of claim 10, wherein said polysaccharide is present in said animal feed in an amount of from 0.01 to 1% by weight.

14. The method of claim 10, wherein said virus is said influenza virus.

15. The method of claim 10, wherein said virus is said herpes virus.

16. The method of claim 10, wherein said virus is said Sendai virus.

17. The method of claim 10, wherein said virus is said subacute sclerosing panencephalitis virus. The method of claim 1, wherein said virus is said influenza virus.

18. The method of claim 10, wherein said polysaccharide is schizophyllan.

19. The method of claim 10, wherein said polysaccharide is scleroglucan.

20. The method of claim 10, wherein said polysaccharide is pendulan.

* * * * *